United States Patent
Takaoka et al.

(10) Patent No.: US 7,375,352 B2
(45) Date of Patent: May 20, 2008

(54) PHOTOMASK DEFECT CORRECTION METHOD EMPLOYING A COMBINED DEVICE OF A FOCUSED ELECTRON BEAM DEVICE AND AN ATOMIC FORCE MICROSCOPE

(75) Inventors: Osamu Takaoka, Chiba (JP); Ryoji Hagiwara, Chiba (JP)

(73) Assignee: SII NanoTechnology Inc. (JP)

( * ) Notice: Subject to any disclaimer, the term of this patent is extended or adjusted under 35 U.S.C. 154(b) by 272 days.

(21) Appl. No.: 11/137,843

(22) Filed: May 25, 2005

(65) Prior Publication Data
US 2005/0285033 A1 Dec. 29, 2005

(30) Foreign Application Priority Data
Jun. 9, 2004 (JP) .............................. 2004-171244

(51) Int. Cl.
*G01N 23/04* (2006.01)
(52) U.S. Cl. ............................. 250/492.2; 250/492.1; 430/4; 430/5
(58) Field of Classification Search ............. 250/492.1, 250/492.2; 430/4, 5; 378/35
See application file for complete search history.

(56) References Cited

U.S. PATENT DOCUMENTS

| | | | |
|---|---|---|---|
| 6,337,479 B1 * | 1/2002 | Kley | 250/234 |
| 6,967,168 B2 * | 11/2005 | Stearns et al. | 438/706 |
| 7,045,780 B2 * | 5/2006 | Kley | 250/306 |
| 2003/0006214 A1 * | 1/2003 | Stearns et al. | 216/66 |
| 2004/0175631 A1 * | 9/2004 | Crocker et al. | 430/5 |

OTHER PUBLICATIONS

Qingliang, et al "Atomic force microscope using a diamond tip: a tool for micro/nano-machining on single crystal silicon surface," Proc. of SPIE, vol. 4601 (2001).*
Morikawa, et al."Defect repair performance using the nanomachining repair technique," Proc. of SPIE, vol. 5130 (2003).*
Boegli, et al. "Electron-beam induced processes and their applicability to mask repair," Proc. of SPIE, vol. 4889 (2002).*

\* cited by examiner

*Primary Examiner*—Robert Kim
*Assistant Examiner*—Michael Maskell
(74) *Attorney, Agent, or Firm*—Adams & Wilks

(57) ABSTRACT

In order to make it possible to improve throughput of AFM scratch processing, enable correction of small defects in clear defect correction with a high degree of precision, and enable correction in a shorter period of time in the event of overcutting by AFM scratch processing, throughput of AFM scratch processing is increased by maximizing high-resolution of the electron beam device and minimizing the time taken in observations using a device incorporating both an electro-optical system and an AFM head in a vacuum, correcting small clear defects with high precision by eliminating portions left over from AFM scratch processing after applying a clear defect correction film using an electron beam while providing light-blocking film raw material, and correction in a short time is made possible by eliminating portions remaining using AFM scratch processing after applying a clear defect correction film using an electron beam while providing light-blocking film raw material also in cases of overcutting in AFM scratch processing.

15 Claims, 3 Drawing Sheets

PHOTOMASK DEFECT CORRECTION METHOD EMPLOYING A COMBINED DEVICE OF A FOCUSED ELECTRON BEAM DEVICE AND AN ATOMIC FORCE MICROSCOPE

BACKGROUND OF THE INVENTION

1. Field of the Invention

The present invention relates to a photomask defect correction method employing a combined device of a focused electron beam device and an atomic force microscope.

2. Description of the Related Art

As fine detailing of patterns becomes smaller, photomask defects of an original plate of a pattern transfer for a wafer to be corrected also become small, and high-precision correction can also be obtained. Further, optical proximity correction (OPC) patterns that are even smaller patterns for correcting optical proximity results so as to increase resolving power have also been introduced which means that it is also necessary to correct defects of OPC patterns that are smaller than these patterns. In addition to defect correction devices employing lasers and focused electron beams of the related art, it is also possible to carry out scratch processing of physically eliminating opaque defects using a diamond tip that makes full use of the high resolving power and superior positional control of an atomic force microscope (for example, "Y. Morikawa, H. Kokubo, M. Nishiguchi, N. Hayashi, R. White, R. Bozak, and L. Terrill, Proc. of SPIE 5130 520-527(2003)).

With AFM scratch processing devices of the related art, low magnifications are observed using an optical microscope and high magnifications are observed using an AFM. There is still a disparity of 10 to 20 µm even if the mask alignment is carried out and the defect scanning device and defect coordinates are linked. It is therefore not possible to know the positions and shapes of defects even when an optical microscope is at maximum magnification because the defects are too small. Image acquisition therefore has to be carried out using an AFM image, which is time-consuming. It is also difficult to search for defects with a field of vision of 40 µm even with an AFM image. Observations are therefore carried out with a field of vision of 10 to 20 µm at positions where defects seem likely to exist and if defects are not found, the observations take place while changing the location, with scratch processing then being carried out upon finding defects. Finding the positions of the defects is therefore more time-consuming than the processing.

The diamond tip is worn after being used in processing and therefore has to be changed. When the tip is changed, it is necessary to always use a dedicated pattern in order to line up the center of the field of vision of the optical microscope and the center of the AFM field of vision. In addition, as described above, the center of the field of vision is offset by approximately 5 µm with respect to the center of the field of vision of the AFM because the magnification rate of the optical microscope is low even in the case of alignment of the centers of the fields of vision. Therefore, even if the centers of the fields of vision are lined up so that observation with a field of vision of 10 µm takes place once, observation then takes place again with a field of vision in the order of 2 µm from the defect being at the center. The load in this field of vision is then increased, and scratch processing is carried out.

Further, with AFM scratch processing, correction is carried out so that a surface eliminated using a special-shaped probe having a vertical cross-section for eliminating opaque defects connected to the pattern becomes vertical. It is therefore necessary to rotate the mask in the direction of the defect. Because of this, it is therefore necessary to carry out mask alignment so as to re-link the defect scanning device and defect coordinates so as to obtain an image and then perform a time-consuming search for defects using an AFM image, which is still more time-consuming.

In addition to opaque defects that are surplus to a pattern in a photomask, there also exist clear defects that are pattern deficiencies, and in theory, it is not possible for the AFM scratch processing device to correct clear defects. In this event, correction takes place using an FIB-CVD film or electron beam CVD film by employing a focused ion beam device (FIB) or electron beam device. However, various problems occur such as thin films of 0.1 µm or less not becoming attached, sagging occurring in the shapes of the films so that transmittance is lowered by a hollow component, and charging up occurring in order to correct a photomask constituted by an insulator so as to cause positional precision to fall. High-precision correction for defects of a level small enough to enable correction using an AFM scratch processor to clear defect correction are then obtained.

In addition to this, at the time of correction using an AFM scratch processing device, in the event that opaque defects are overcut, it is not possible to achieve anything by just using an AFM scratch processing device that can only perform elimination processing. In this case, correction of overcut portions takes place using a clear defect correction function of an FIB or electron beam device but high-precision correction of defects of a level small enough to enable correction using an AFM scratch processor was not possible. Further, in the related art, separate devices exist, AFM scratch processing devices operating in the atmosphere and FIB and electronic beam devices requiring a vacuum. Because of this, when both AFM scratch processing devices and FIB and electronic beam devices requiring a vacuum are employed, it is necessary to transfer a sample between each device. Only defect positions are required by respective devices where samples are transferred. In cases where it is necessary to alternately use AFM scratch processing devices and FIB and electron beam devices a plurality of times, the number of times it is necessary to output positions of defects using time-consuming AFM scratch processing increases, which causes operation time to increase substantially. Further, at the time of use of the FIB and electron beam device, time is required every time vacuuming takes place and to await the release of the atmosphere, re-alignment of the mask is necessary every time a mask is replaced, which is an extremely time-consuming operation.

In order to resolve the aforementioned problems, the present invention is advantageous in increasing throughput of AFM scratch processing, and enabling small clear defects to be corrected with a high degree of precision in clear defect correction. Further, in the event of over-removal in AFM scratch processing, correction is possible over a short time.

SUMMARY OF THE INVENTION

In order to resolve the aforementioned problems, a device is employed that combines an electron beam device having the features of high resolution, short observation time, little damage imparted on a sample when observing an image and clear defect correction capabilities and an AFM scratch processor having the feature of being capable of precise dark defect correction. The following methods are then carried out using this device.

Position alignment after changing an AFM probe is such that a deepest position of an impression of a probe resulting from the probe being pressed in is observed using a focused electron beam at the center of the field of vision (viewing field) of an AFM after conversion, and a distance between this position and a center of a field of vision (viewing field) of a focused electron beam is taken as an offset amount between an atomic force microscope probe and a focused electron beam so as to correct shifts in a tip fitting position. Namely, the scanning range of the AFM and the focused electron beam is given an offset in such a manner that the center of the field of vision of the focused electron beam and the center of the field of vision of the AFM are offset.

Defects are observed at a high-resolution using a focused electron beam so as to obtain the position and shape of defects to be corrected in order to extract the positions of defects at high-speed using an AFM scratch processor. The position of defects is then extracted using the AFM scratch processor based on this information, and the defects are subjected to scratch processing AFM.

With clear defect correction, first, a clear defect is irradiated with a focused electron beam while providing light-blocking layer source gas so that a light-blocking film is deposited on a clear defect region protruding from a normal pattern. After that, the protruding portion is removed by AFM scratch processing as with the opaque defect correction. It is therefore possible to correct small clear defects with a high degree of precision in this manner.

At the time of correcting opaque defects protruding from the normal pattern using AFM scratch processing, a light-blocking film is deposited in such a manner that, with regards to of overcutting to an extent of digging in as far as the pattern layer, the overcut portion is made to protrude from the normal pattern using a focused electron beam while supplying light-blocking film source gas. The protruding portion is then cut away so as to be restored in the same way as for opaque defect correction.

By observing using a focused electron beam it is therefore possible to reduce the number of times of image observation using AFM where position alignment taking five to ten minutes each time after changing a tip takes place. This means that time-consuming changing of the tip and subsequent alignment of the tip can be made to happen more quickly. A device is used where an electron beam and an AFM are combined within a vacuum. Evacuating the vacuum and releasing the air take in the order of ten minutes. However, high-magnification observations depend on time-consuming AFM observations. It is therefore possible to make the total correction time short compared with conventional systems of the related art composed of an AFM and an optical microscope.

It is possible to omit time-consuming AFM imaging by carrying out determinations in a direction (rotational direction of the stage) necessary for a vertical cross-section. This means it is possible for the total correction time to be made short even if the vacuum exhaust time and the atmosphere discharge time are time-consuming.

It is also possible to omit the AFM imaging that took time in the related art because the calculation of a shift compensation amount for an angle of fitting to the vertical surface of the processing tip is carried out using a secondary electron image of a focused electron beam. It is therefore possible to make the total time short. The extent of shift of an angle of fitting to the vertical surface of the processing tip is corrected using rotation of the stage. The XY stage is then moved so as to correct shifts in the XY position. Extraction of the defect position is then carried out using the secondary electron image of the focused electron beam. It is therefore possible to omit the time-consuming AFM imaging of the related art and total time can be made shorter.

A distinction from a unitary AFM scratch processor is that a light-blocking film is attached using an electronic beam CVD and clear defect correction is therefore also possible. After attaching the light-blocking film, this is removed using AFM scratch processing. It is therefore also possible to correct small defects and high-precision correction of the same order as for AFM scratch opaque defect correction can be carried out.

By using a device where the focused electron beam and the AFM scratch unit are in a vacuum, it is possible to shorten the time of taking out and inserting the mask and performing mask alignment, and correct an overcut location using opaque defect correction for AFM scratch processing in a shorter period of time compared with the case of other devices of the related art.

DETAILED DESCRIPTION OF THE PREFERRED EMBODIMENTS

The following is a description of an embodiment of the present invention.

Figure 1:
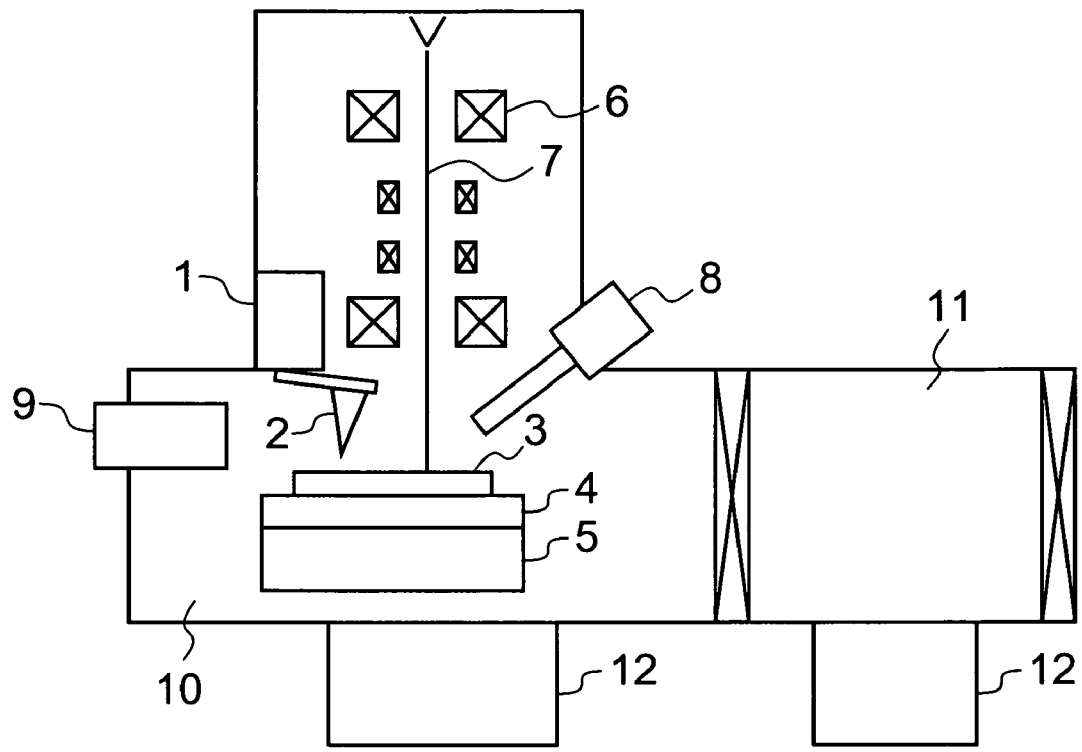
FIG. 1 is an outline cross-sectional view illustrating an apparatus for carrying out the method of the present invention.

FIG. 1 shows a combined device of a focused electron beam device and AFM used in the present invention. A photomask 3 for which a defect has been found using a defect scanning device is introduced into a preliminary chamber or pre-chamber 11 of a device combining an electro-optical system 6 and an atomic force microscope (AFM) head 1 within a container having a vacuum evacuation system 12, and preliminary evacuation is carried out. When a vacuum is created in the preliminary chamber 11, the photomask 3 is moved into a work chamber 10 and placed on a rotating stage 4 supported on an XY stage 5. In the combined device, the work chamber 10 is common to and shared by the focused electron beam device and the AFM. An alignment mark of the mask is then observed at a high-magnification by detecting secondary electrons generated from the sample owing to irradiation of the focused electron beam 7 with the secondary electron detector 9, and mask alignment (alignment of the defect scanning device and coordinate starting points) is carried out. Alignment mark alignment can also be carried out at a higher precision than in the case of alignment using an optical microscope, and can be carried out in a short period of time in the case of AFM alignment. The XY stage 5 is then moved to the position of a defect after mask alignment.

Figure 2:
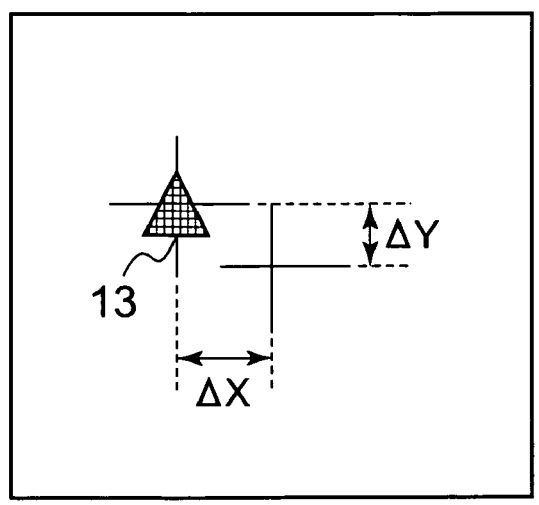
FIG. 2 is a view illustrating a method for aligning the position of a tip after changing a tip.

In the event that it is necessary to change a probe tip 2 provided at the distal end of a cantilever of the AFM during processing, the XY stage 5 is moved to the position of the AFM head 1, and the probe tip is gently pushed against the sample at the center of the field of vision (viewing field) of the AFM to form an impression of the tip 2 that constitutes a reference position 13 as shown in FIG. 2 prior to changing the tip. Next, the XY stage 5 is moved to the center of the field of vision (viewing field) of the focused electron beam 7, a high magnification secondary electron image is taken, a new position for the tip 2 is obtained from the reference position 13 of the impression of the tip, the extent of offset ΔX, ΔY of the AFM and the focused electron beam is corrected, and correction of the position of the tip is carried out. Namely, the center of the field of vision of the AFM microscope before changing the tip and after changing the tip shift due to errors in fitting the tip. It can therefore be understood to what extent the position of the probe is shifted after changing by pressing in the tip at the center of the field of vision before changing the tip, and the scanning range is offset in such a manner that the center of the field of vision of the AFM coincides before changing the tip and after changing the tip. Position correction for the tip after changing the tip can therefore be carried out in a shorter time than for the related art because there is no observation step using an AFM. The precision of position alignment is therefore improved compared to alignment of the position of the optical microscope because the position is measured using a secondary electron image of high magnification. It is also possible to obtain the amount of shift in the fitting angle of the vertical cross-sectional surface from the shape of the indent.

The defect is therefore observed using a secondary image of high-resolution, and the shape of the defect can be understood. In the event of isolated opaque defects, processing takes place using a processing tip that is symmetrical in shape. In the event that an opaque defect is adjacent to a pattern, the rotating stage 4 is rotated about an axis perpendicular to an upper surface of the rotating stage 4 in such a manner that a defect pattern side surface becomes parallel to a processing surface of the processing tip 2. An amount of correction for the XY direction of the XY stage 5 is calculated from the angle of rotation and position correction is carried out. A defect is then searched out using a focused electron beam 7 and eliminated using scratch processing of the processing tip 2 having a perpendicular cross-sectional surface.

However, there may also be cases where a defect cannot be found at this position even when the amount of correction for the XY stage 5 is calculated from the angle of rotation and the position corrected because of shifts in the axis of 5 to 20 μm at the rotating stage. This vicinity may therefore be searched using a time-consuming AFM image using an AFM scratch processor of the related art or the mask alignment may be re-taken and scratch processing may then be carried out from searching out defects in a time-consuming manner using the AFM image. However, in this application, defect searching is carried out after correction of the rotation of the stage using an image of a focused electron beam for which time taken for imaging is overwhelmingly shorter than for AFM. It is therefore possible to also search out defects in a short time even in cases of searching the vicinity when a defect is not found at a corrected position or in cases where mask alignment is performed once in a rotated state.

Figure 3A:
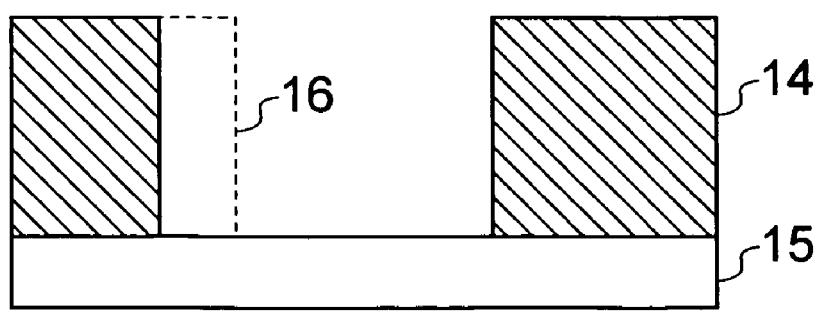
FIGS. 3A-3C are cross-sectional views illustrating a correction method in the case of correcting a clear defect or in the case of correction a portion that has been overcut in a scratch process.
Figure 3B:
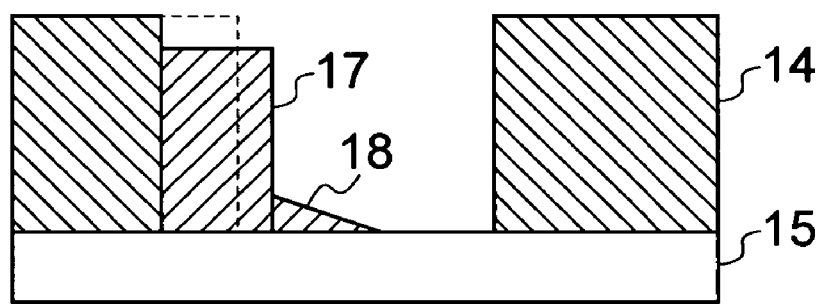
Figure 3C:
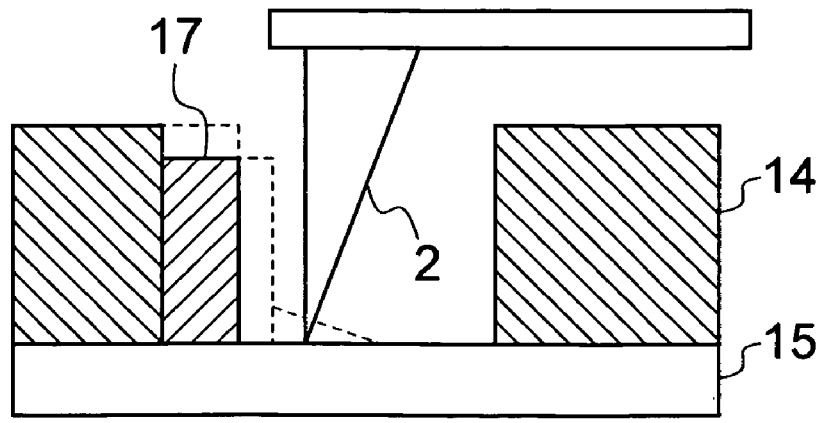

A description is given of a correction method for the case where defects are clear defects using FIGS. 3A-3C. In FIG. 3A there is a clear defect 16 where part of light-blocking film 14 on glass substrate 15 is lacking. The XY stage 5 is moved in such a manner that a clear defect 16 approaches the center of the field of vision of the focused electron beam in FIG. 3A. A light-blocking film 17 is applied in such a manner as to protrude out from a clear defect 16 by using a focused electron beam while light-blocking source gas flows in from the gas supply system 8 in FIG. 3B. Next, the stage is moved so that the light-blocking film 17 comes into the center of the field of vision of the AFM, and excess light-blocking film and hollow component 18 of the light-blocking film 17 is eliminated using AFM scratch processing in FIG. 3C. It is therefore possible to carry out scratch processing in such a manner that there is almost no damage to the foundation because AFM scratch processing has superior height controllability.

Even in the event that overcutting occurs in opaque defect correction due to AFM scratch processing, defect correction using the same method as shown above is adopted for the overcut portions. Repeated processing is also possible because the transmittance of the AFM scratch processing imaging and the focused electron beam imaging does not fall.

Figure 4A:
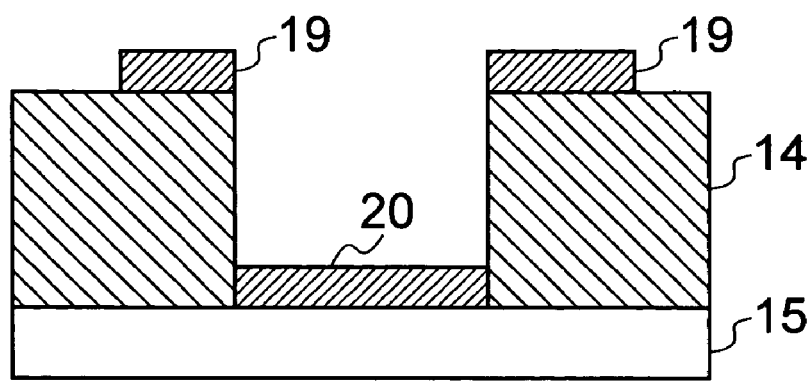
FIGS. 4A-4B are outline cross-sections illustrating a case where contamination of a glass portion accompanying focused electron beam imaging is eliminated using AFM scratch processing.
Figure 4B:
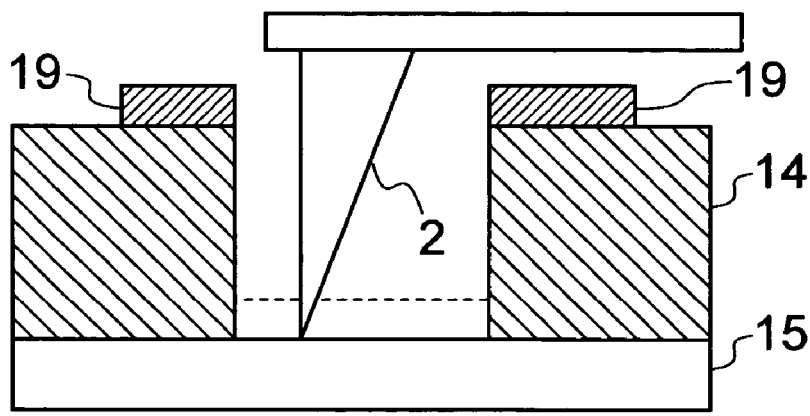

During focused electron beam imaging, in the event that there is a reaction with residual gas in the vacuum so that contamination 19 or 20 accumulates on the light-blocking film 14 or photomask substrate (glass substrate) 15 during focused electron beam imaging, as shown in FIG. 4A, it is then possible to prevent the transmittance from being lowered through the attachment of contamination by removing contamination 20 on the glass substrate 15 using AFM scratch processing using a tip 2 that is harder than the contamination, as shown in FIG. 4B.

What is claimed is:

1. A photomask defect correction method employing a combined device of a focused electron beam device and an atomic force microscope, comprising the steps of:

pressing a processing tip of an atomic force microscope onto a sample in such a manner as to form an impression;

observing the impression using a focused electron bean device;

obtaining an extent of offset of a focused electron bean and an atomic force microscope from a shift in position from a center of a field of vision of a focused electron beam for the impression so as to correct a shift in the field of vision;

observing a defect of a photomask using the focused electron beam device;

positioning the photomask defect in the center of the field of vision of the atomic force microscope based on the extent of offset; and correcting the photomask defect using the atomic force microscope.

2. A photomask detect correction method employing a combined device of a focused electron beam device and an atomic force microscope, comprising the steps of:

observing an opaque defect of a photomask supported on a rotatable stage using a focused electron beam and obtaining information concerning the opaque defect including information of the defect position, defect type, defect direction and defect size; and correcting the opaque defect, using an atomic force microscope, by rotating the rotatable stage to position the opaque defect relative to a probe tip of the atomic force microscope based on the obtained information of the defect position, defect type, defect direction and defect size.

3. A photomask defect correction method employing a combined device of a focused electron beam device and an atomic force microscope, comprising the steps of:
placing a photomask having a defect on an XY stage;
pressing a processing tip of an atomic force microscope onto the photomask so as to form an impression before correcting the photomask defect;
observing the impression using a focused electron ben and obtaining an angle of a side of the impression that corresponds to a processing surface of the processing tip with respect to an X-axis or Y-axis of the XY stage;
adjusting the angle of the processing tip in such a manner that the processing surface thereof becomes parallel with either of the X or Y axes; and thereafter
correcting the photomask defect using the processing surface of the processing tip of the atomic force microscope.

4. A photomask defect correction method employing a combined device of a focused electron beam device and an atomic force microscope, comprising the steps of:
depositing an opaque film by chemical vapor deposition using a focused electron beam at a clear defect portion in such a manner that the opaque film protrudes from a normal pattern; and
eliminating the protruding portion using an atomic force microscope;
wherein the depositing and eliminating steps are carried out in the same work chamber.

5. A photomask defect correction method employing a combined device of a focused electron beam device and an atomic force microscope, comprising the steps of:
cutting an opaque detect protruding from a normal pattern using a tip of an atomic force microscope;
depositing an opaque film at an over-cut portion so as to protrude from the normal pattern using chemical vapor deposition employing a focused electron beam when over-cutting takes place so as to encroach as far as the normal pattern; and
lining up the protruding portion with the normal pattern using the atomic force microscope tip and removing the protruding portion;
wherein the eliminating, depositing and lining up steps are all carried out in the same work chamber.

6. A method employing a combined device of a focused electron beam device and an atomic force microscope, comprising the steps of:
observing an area of a photomask within a vacuum using a focused electron beam; and
removing contamination deposited on the photomask substrate owing to reaction of the focused electron beam with residual gas within the vacuum using an atomic force microscope.

7. A photomask defect correction method according to claim 3; wherein the adjusting step is carried out by rotating the XY stage to position the processing surface of the processing tip in parallel with either of the X or Y axes.

8. A method of processing a sample supported on an XY stage in a work chamber shared by an atomic force microscope and a focused electron bean device, comprising the steps:
observing the sample in the work chamber using the focused electron beam device to locate a prescribed area to be processed; and
processing the prescribed area of the sample in the work chamber using the atomic force microscope without removing the sample from the work chamber between the observing and processing steps.

9. A method according to claim 8; wherein the prescribed area is a sample defect; and the processing step comprises correcting the sample defect.

10. A method according to claim 9; wherein the sample defect is an opaque detect; and the processing step comprises removing the opaque defect by scratch processing using a probe tip of the atomic force microscope.

11. A method according to claim 9; wherein the sample defect is a clear defect; and the processing step comprises depositing a light-blocking film on the clear defect by a chemical vapor deposition using the focused electron beam device, and removing excess portions of the deposited light-blocking film by scratch processing using a probe tip of the atomic force microscope.

12. A method according to claim 8; further including the step of removing contamination deposited on the sample, created by reaction of a focused electron beam of the focused electron beam device with residual gas within the work chamber, by scratch processing using a probe tip of the atomic force microscope.

13. A method according to claim 8; further including, before the processing step, the steps of pressing a probe tip of the atomic force microscope onto the sample to form an impression of the probe tip, observing the impression using the focused electron beam device, determining an extent of offset of the impression from the center of a viewing field of the focused electron beam device, and adjusting the scanning range of the atomic force microscope based on the determined offset.

14. A method according to claim 13; further including the steps of determining an angle between a side of the impression that corresponds to a processing surface of the probe tip and an X-axis or Y-axis of the XY stage, and rotating the XY stage to position the processing surface of the probe tip in parallel with the X-axis or Y-axis of the XY stage.

15. A method of matching the viewing fields of an atomic force microscope and a focused electron beam device, comprising the steps of:
providing an atomic force microscope and a focused electron beam device that share a common work chamber;
pressing a probe tip of the atomic force microscope onto a sample in the work chamber to form an impression of the probe tip at a center of a viewing field of the atomic force microscope;
observing the impression using a focused electron beam of the focused electron beam device;
determining an extent of offset of a center of a viewing field of the focused electron beam device and the center of the viewing field of the atomic force microscope based on the observed impression; and
adjusting the scanning range of the atomic force microscope based on the determined offset.

* * * * *